US011912726B2

(12) United States Patent
Schneider et al.

(10) Patent No.: US 11,912,726 B2
(45) Date of Patent: *Feb. 27, 2024

(54) PT-XANTHENE-IODINE COMPLEX AND PT-XANTHENE-BROMINE COMPLEX

(71) Applicant: EVONIK OPERATIONS GMBH, Essen (DE)

(72) Inventors: Carolin Schneider, Monheim am Rhein (DE); Ralf Jackstell, Rostock (DE); Matthias Beller, Ostseebad Nienhagen (DE); Robert Franke, Marl (DE)

(73) Assignee: EVONIK OXENO GMBH & CO. KG, Marl (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/064,952

(22) Filed: Dec. 13, 2022

(65) Prior Publication Data

US 2023/0192742 A1 Jun. 22, 2023

(30) Foreign Application Priority Data

Dec. 17, 2021 (EP) .................................. 21215337

(51) Int. Cl.
*C07F 15/00* (2006.01)
*C07F 9/28* (2006.01)

(52) U.S. Cl.
CPC ................. *C07F 15/0086* (2013.01)

(58) Field of Classification Search
CPC ..... C07F 15/0086; C07F 9/28; B01J 31/2457; C07C 45/505
USPC .................. 549/212; 502/171, 185
See application file for complete search history.

(56) References Cited

U.S. PATENT DOCUMENTS

| | | |
|---|---|---|
| 2010/0048959 A1 | 2/2010 | Sigl et al. |
| 2010/0286440 A1 | 11/2010 | Kimmich et al. |
| 2019/0211040 A1 | 7/2019 | Boerner et al. |
| 2023/0191384 A1 | 6/2023 | Schneider et al. |
| 2023/0191385 A1 | 6/2023 | Schneider et al. |
| 2023/0192581 A1 | 6/2023 | Schneider et al. |
| 2023/0192582 A1 | 6/2023 | Schneider et al. |
| 2023/0192583 A1 | 6/2023 | Schneider et al. |
| 2023/0192584 A1 | 6/2023 | Schneider et al. |
| 2023/0192740 A1 | 6/2023 | Schneider et al. |
| 2023/0192741 A1 | 6/2023 | Schneider et al. |
| 2023/0192743 A1 | 6/2023 | Schneider et al. |

FOREIGN PATENT DOCUMENTS

| | | |
|---|---|---|
| TW | 200835678 A | 9/2008 |
| TW | 201041844 A | 12/2010 |
| WO | 2010/129030 A2 | 11/2010 |
| WO | 2017/191310 A1 | 11/2017 |

OTHER PUBLICATIONS

U.S. Appl. No. 18/064,945, Schneider et al., filed Dec. 13, 2022.
U.S. Appl. No. 18/064,946, Schneider et al., filed Dec. 13, 2022.
U.S. Appl. No. 18/064,947, Schneider et al., filed Dec. 13, 2022.
U.S. Appl. No. 18/064,948, Schneider et al., filed Dec. 13, 2022.
U.S. Appl. No. 18/064,949, Schneider et al., filed Dec. 13, 2022.
U.S. Appl. No. 18/064,950, Schneider et al., filed Dec. 13, 2022.
U.S. Appl. No. 18/064,953, Schneider et al., filed Dec. 13, 2022.
U.S. Appl. No. 18/064,955, Schneider et al., filed Dec. 13, 2022.
U.S. Appl. No. 18/064,958, Schneider et al., filed Dec. 13, 2022.
Botteghi, C. et al. Synthesis of 2-chromanol by hydroformylation of 2-hydroxystyrene derivatives. Journal of Molecular Catalysis A: Chemical 200. 2003. pp. 147-156.
European Search Report dated May 30, 2022 for European Patent Application No. 21215337.3 (8 pages in German with English Translation).
Petöcz, G., et al. Xantphos as cis- and trans-chelating ligand in square-planar platinum(II) complexes. Hydroformylation of styrene with platinum-xantphos-tin(II)chloride system. Journal of Organometallic Chemistry. 2004. vol. 689, No. 7, pp. 1188-1193.
European Office Action dated Aug. 21, 2023 for European Patent Application No. 21215337.3 (5 pages in German with English translation).
Van der Veen, Lars A., et al. Wide bite angle amine, arsine and phosphine ligands in rhodium- and platinum/tin-catalysed hydroformylation. J Chem. Soc., Dalton Trans. 2000 pp. 2105-2112.
Meessen, Patric, et al. Highly regioselective hydroformylation of internal, functionalized olefins applying PT* Sn complexes with large bite angle diphosphines. Journal of Organometallic Chemistry 551. 1998. vol. 551 pp. 165-170.
Taiwan Ofice Action and Search Report dated Aug. 25, 2023 for Taiwan Patent Application No. 111147943 (4 pages in Chinese; 3 pages English Translation).
Translation of First Examination Report for Saudi Arabia Patent Application No. 122440887, dated Jun. 2023 (3 pages).
Duren, van, R. Platinum catalyzed hydroformylation. [Phd—Thesis 1 (Research TU/e / Graduation TU/e), Chemical Engineering and Chemistry]. Technische Universiteit Eindhoven. Jan. 1, 2004. 119 pages.
Zhang, Yang et al. Binuclear Pd(I)-Pd(I) Catalysis Assisted by Iodide—Ligands for Selective Hydroformylation of Alkenes and Alkynes. American Chemical Society. Oct. 9, 2020. vol. 142, pp. 18251-18265.

*Primary Examiner* — Charanjit Aulakh
(74) *Attorney, Agent, or Firm* — Smith, Gambrell & Russell, LLP

(57) ABSTRACT

Pt-xanthene-iodine complex and Pt-xanthene-bromine complex, and use thereof for catalysis of a hydroformylation reaction.

12 Claims, No Drawings

PT-XANTHENE-IODINE COMPLEX AND PT-XANTHENE-BROMINE COMPLEX

PT-XANTHENE-IODINE COMPLEX AND PT-XANTHENE-BROMINE COMPLEX

The present invention relates to a Pt-xanthene-iodine complex and Pt-xanthene-bromine complex, and the use thereof for catalysis of a hydroformylation reaction.

C. Botteghi et al., Journal of Molecular Catalysis A: Chemical 200, (2003), 147-156 describes the use of Pt(Xantphos)$Cl_2$ for hydroformylation of 2-tosyloxystyrene.

The problem addressed by the present invention is that of providing a novel complex. The complex here is to afford an enhanced yield in the catalysis of hydroformylation reactions compared to the complex of Pt with $Cl_2$ described in the prior art.

This object is achieved by a complex according to Claim 1.

Complex comprising:
a) Pt;
b) a ligand conforming to the formula (I):

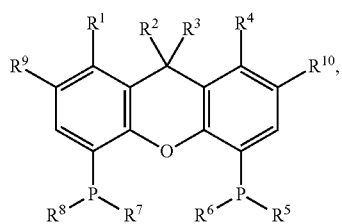

(I)

where $R^1$, $R^2$, $R^3$, $R^4$, $R^5$, $R^6$, $R^7$, $R^8$ are selected from: —H, —($C_1$-$C_{12}$)-alkyl, —($C_6$-$C_{20}$)-aryl, and $R^9$, $R^{10}$ are selected from: —($C_1$-$C_{12}$)-alkyl, —($C_6$-$C_{20}$)-aryl, and, if $R^1$, $R^2$, $R^3$, $R^4$, $R^5$, $R^6$, $R^7$, $R^8$, $R^9$, $R^{10}$ are —($C_6$-$C_{20}$)-aryl, the aryl ring may have substituents selected from: —($C_1$-$C_{12}$)-alkyl, —O—($C_1$-$C_{12}$)-alkyl; c) an iodine ligand or bromine ligand.

The expression ($C_1$-$C_{12}$)-alkyl encompasses straight-chain and branched alkyl groups having 1 to 12 carbon atoms. These are preferably ($C_1$-$C_8$)-alkyl groups, more preferably ($C_1$-$C_6$)-alkyl, most preferably ($C_1$-$C_4$)-alkyl.

Suitable ($C_1$-$C_{12}$)-alkyl groups are especially methyl, ethyl, propyl, isopropyl, n-butyl, iso-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression ($C_6$-$C_{20}$)-aryl encompasses mono- or polycyclic aromatic hydrocarbyl radicals having 6 to 20 carbon atoms. These are preferably ($C_6$-$C_{14}$)-aryl, more preferably ($C_6$-$C_{10}$)-aryl.

Suitable ($C_6$-$C_{20}$)-aryl groups are especially phenyl, naphthyl, indenyl, fluorenyl, anthracenyl, phenanthrenyl, naphthacenyl, chrysenyl, pyrenyl, coronenyl. Preferred ($C_6$-$C_{20}$)-aryl groups are phenyl, naphthyl and anthracenyl.

In one embodiment, $R^2$, $R^3$, $R^5$, $R^6$, $R^7$, $R^8$ are selected from: —($C_1$-$C_{12}$)-alkyl, —($C_6$-$C_{20}$)-aryl.

In one embodiment, $R^5$, $R^6$, $R^7$, $R^8$ are —($C_6$-$C_{20}$)-aryl.

In one embodiment, $R^5$ and $R^6$ are different radicals and $R^7$ and $R^8$ are different radicals.

In one embodiment, $R^2$ and $R^3$ are —($C_1$-$C_{12}$)-alkyl.

In one embodiment, $R^2$ and $R^3$ are —$CH_3$.

In one embodiment, $R^1$ and $R^4$ are —H.

In one embodiment, $R^9$ and $R^{10}$ are —($C_1$-$C_{12}$)-alkyl.

In one embodiment, $R^9$ and $R^{10}$ are —$^t$Bu.

In one embodiment, the ligand conforming to the formula (I) has the structure (1):

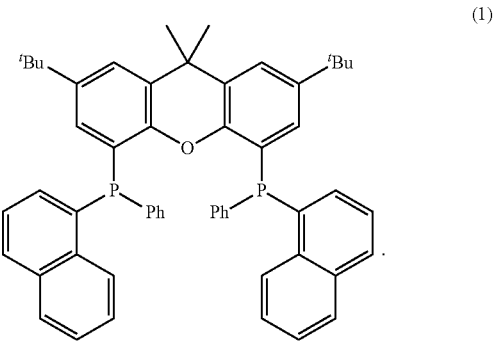 [SMILES: CC(C)(C)c1cc(P(c2ccccc2)c2cccc3ccccc23)c2c(c1)C(C)(C)c1cc(C(C)(C)C)cc(P(c3ccccc3)c3cccc4ccccc34)c1O2]

(1)

In one embodiment, the complex has exactly one ligand conforming to the formula (I).

In one embodiment, the complex has at least two iodine ligands.

In one embodiment, the complex has exactly two iodine ligands.

In one embodiment, the complex has at least two bromine ligands.

In one embodiment, the complex has exactly two bromine ligands.

As well as the complex per se, the use thereof for catalysis of a hydroformylation reaction is also claimed.

Use of a complex as described above for catalysis of a hydroformylation reaction.

The invention shall be elucidated in more detail hereinbelow with reference to working examples.

EXPERIMENTAL DESCRIPTION

A vial was charged with $PtX_2$ (X=halogen), ligand, and an oven-dried stirrer bar. The vial is then sealed with a septum (PTFE-coated styrene-butadiene rubber) and phenolic resin cap.

The vial is evacuated and refilled with argon three times. Toluene and 1-octene were added to the vial using a syringe. The vial was placed in an alloy plate, which was transferred to an autoclave of the 4560 series from Parr Instruments under an argon atmosphere. After purging the autoclave three times with $CO/H_2$, the synthesis gas pressure was increased to 40 bar at room temperature. The reaction was conducted at 80° C. for 18 h. On termination of the reaction, the autoclave was cooled to room temperature and cautiously decompressed. Yield and selectivity were determined by GC analysis.

Variation of the Halogen

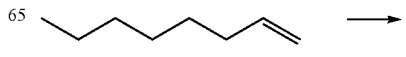

-continued

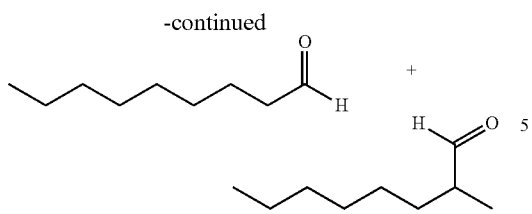

Reaction conditions:
1.0 mmol of 1-octene, 0.5 mol % of PtX$_2$, 2.0 equivalents of ligand (1), solvent: toluene, p(CO/H$_2$): 40 bar, T: 80° C., t: 18 h.
Yields:

| Ligand | Halogen | Yield [%] |
|---|---|---|
| 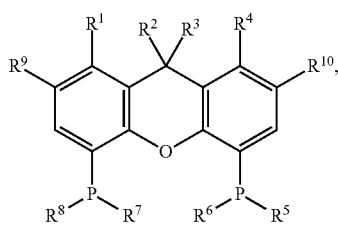 (1) | I/Br/Cl | 96/24/0 |

As the experimental results show, the object is achieved by the complex according to the invention.

The invention claimed is:

1. A complex comprising:
a) Pt;
b) a ligand conforming to the formula (I):

(I)

R$^1$  R$^2$ R$^3$  R$^4$
R$^9$            R$^{10}$,
         O
  R$^8$  P  R$^7$   R$^6$  P  R$^5$ where R$^1$, R$^2$, R$^3$, R$^4$, R$^5$, R$^6$, R$^7$ and R$^8$ are selected from:
—H, —(C$_1$-C$_{12}$)-alkyl or —(C$_6$-C$_{20}$)-aryl, and
R$^9$ and R$^{10}$ are selected from: —(C$_1$-C$_{12}$)-alkyl or —(C$_6$-C$_{20}$)-aryl, and, if R$^1$, R$^2$, R$^3$, R$^4$, R$^5$, R$^6$, R$^7$, R$^8$, R$^9$ and R$^{10}$ are —(C$_6$-C$_{20}$)-aryl, the aryl ring may have substituents selected from: —(C$_1$-C$_{12}$)-alkyl or —O—(C$_1$-C$_{12}$)-alkyl;
c) an iodine ligand or bromine ligand.
2. The complex according to claim 1,
where R$^2$, R$^3$, R$^5$, R$^6$, R$^7$ and R$^8$ are selected from: —(C$_1$-C$_{12}$)-alkyl or —(C$_6$-C$_{20}$)-aryl.
3. The complex according to claim 1
where R$^5$, R$^6$, R$^7$ and R$^8$ are —(C$_6$-C$_{20}$)-aryl.
4. The complex according to claim 1,
where R$^2$ and R$^3$ are —(C$_1$-C$_{12}$)-alkyl.
5. The complex according to claim 1,
where R$^1$ and R$^4$ are —H.
6. The complex according to claim 1,
where R$^9$ and R$^{10}$ are —(C$_1$-C$_{12}$)-alkyl.
7. The complex according to claim 1,
wherein the ligand conforming to the formula (I) has the structure (1):

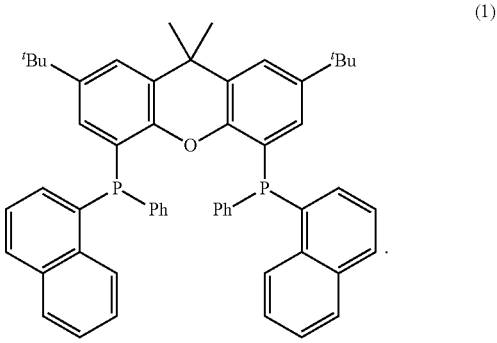 [SMILES: CC(C)(C)c1cc(P(c2ccccc2)c2cccc3ccccc23)c2c(c1)C(C)(C)c1cc(C(C)(C)C)cc(P(c3ccccc3)c3cccc4ccccc34)c1O2]

8. The complex according to claim 1,
wherein the complex has exactly one ligand conforming to the formula (I).
9. The complex according to claim 1,
wherein the complex has at least two iodine ligands.
10. The complex according to claim 9,
wherein the complex has exactly two iodine ligands.
11. The complex according to claim 1,
wherein the complex has at least two bromine ligands.
12. The complex according to claim 11,
wherein the complex has exactly two bromine ligands.

* * * * *